United States Patent
Oda et al.

(10) Patent No.: US 11,186,557 B2
(45) Date of Patent: Nov. 30, 2021

(54) METHOD FOR PURIFYING PURE THIOFLAVIN T, METHOD FOR PRODUCING PURE THIOFLAVIN T, COMPOSITION INCLUDING THIOFLAVIN T, AND AMYLOID DETECTION METHOD

(71) Applicant: HAMAMATSU PHOTONICS K.K., Hamamatsu (JP)

(72) Inventors: Akinori Oda, Hamamatsu (JP); Hiroshi Satozono, Hamamatsu (JP); Tomomi Shinke, Hamamatsu (JP); Yohei Takata, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 351 days.

(21) Appl. No.: 15/763,926

(22) PCT Filed: Aug. 15, 2016

(86) PCT No.: PCT/JP2016/073846
§ 371 (c)(1),
(2) Date: Mar. 28, 2018

(87) PCT Pub. No.: WO2017/056758
PCT Pub. Date: Apr. 6, 2017

(65) Prior Publication Data
US 2018/0273498 A1   Sep. 27, 2018

(30) Foreign Application Priority Data
Sep. 29, 2015   (JP) .............................. JP2015-191312

(51) Int. Cl.
*G01N 33/52* (2006.01)
*G01N 21/64* (2006.01)
*C07D 277/66* (2006.01)
*G01N 33/68* (2006.01)

(52) U.S. Cl.
CPC ......... *C07D 277/66* (2013.01); *G01N 21/643* (2013.01); *G01N 33/52* (2013.01); *G01N 33/6893* (2013.01); *G01N 2333/4709* (2013.01); *Y10T 436/145555* (2015.01); *Y10T 436/255* (2015.01)

(58) Field of Classification Search
CPC ......... C07D 277/66; G01N 2333/4709; G01N 33/52; G01N 33/68; G01N 33/6893; G01N 21/64; G01N 21/643; Y10T 436/145555; Y10T 436/17; Y10T 436/18; Y10T 436/19; Y10T 436/25; Y10T 436/25375; Y10T 436/255

USPC ........ 436/96, 106, 119, 124, 164, 172, 174, 436/177, 178; 422/82.05, 82.08, 527, 422/534, 535
See application file for complete search history.

(56) References Cited

U.S. PATENT DOCUMENTS

| | | | |
|---|---|---|---|
| 5,486,460 A | 1/1996 | Townsend | |
| 10,564,153 B2* | 2/2020 | Davis | ............ G01N 33/689 |
| 2006/0194821 A1* | 8/2006 | Lansbury | ............ A61P 43/00 514/263.23 |
| 2009/0286745 A1* | 11/2009 | Zurdo | ............ C07K 5/0817 514/10.3 |
| 2012/0070374 A1* | 3/2012 | Gjermund | ............ C07D 277/66 424/1.89 |
| 2018/0273497 A1* | 9/2018 | Satozono | ............ G01N 33/6896 |

FOREIGN PATENT DOCUMENTS

| | | |
|---|---|---|
| JP | 2000-198781 A | 7/2000 |
| JP | 2017-066066 A | 4/2017 |
| WO | WO-2006/089221 A2 | 8/2006 |
| WO | WO-2008/003943 A2 | 1/2008 |

OTHER PUBLICATIONS

International Preliminary Report on Patentability dated Apr. 12, 2018 for PCT/JP2016/073846.
LeVine III, H, "Thioflavine T interaction with synthetic Alzheimer's disease β-amyloid peptides: Detection of amyloid aggregation in solution", Protein Science, 1993, vol. 2, p. 404-p. 410.
Naik,L.R., "Steady-state and time-resolved emission studies of Thioflavin-T", Journal of Photochemistry and Photobiology A: Chemistry, 2009, vol. 204, p. 161-p. 167.
Freire, S. et al., "Photophysical study of Thioflavin T as fluorescence marker of amyloid fibrils," Dyes and Pigments, vol. 110, 2014, pp. 97-105.
Groenning, M., "Binding mode of Thioflavin T and other molecular probes in the context of amyloid fibrils-current status," J. Chem. Biol., vol. 3(1), 2010, pp. 1-18.
Hsu, J.C.C. et al., "Thioflavin T and Its Photoirradiative Derivatives: Exploring Their Spectroscopic Properties in the Absence and Presence of Amyloid Fibrils," The Journal of Physical Chemistry B, vol. 117, 2013, pp. 3459-3468.

(Continued)

*Primary Examiner* — Maureen Wallenhorst
(74) *Attorney, Agent, or Firm* — Faegre Drinker Biddle & Reath LLP

(57) ABSTRACT

The present invention relates to a method for purifying pure thioflavin T in having a step of preparing a thioflavin T solution in which crude thioflavin T is dissolved in a polar solvent, a step of bringing the thioflavin T solution into contact with a non-polar polymeric porous body, and a step of separating the thioflavin T solution after the contact from the non-polar polymeric porous body.

6 Claims, 11 Drawing Sheets

(56) References Cited

OTHER PUBLICATIONS

Voropai, E.S. et al., "Spectral Properties of Thioflavin T and Its Complexes with Amyloid Fibrils," Journal of Applied Spectroscopy, vol. 70, No. 6, 2003, pp. 868-874.
"Kagaku Binran, Oyo Kagaku Hen 6th edition," 2003, I, pp. 182-183, pp. 1113-1115, including partial English translation.
Chemical Society of Japan, "4th edition, Experimental Chemistry Course 1, Basic Operations I, 2nd print," Maruzen Co., Ltd., Apr. 5, 1996, pp. 191-193, including Partial English-language translation.
Chemical Society of Japan, "5th edition, Experimental Chemistry Course 20-1, Analytical Chemistry, 2nd print," Maruzen Co., Ltd., May 15, 2007, pp. 61-64, including Partial English-language translation.

* cited by examiner (A)

(B)

(A)

(B)

METHOD FOR PURIFYING PURE THIOFLAVIN T, METHOD FOR PRODUCING PURE THIOFLAVIN T, COMPOSITION INCLUDING THIOFLAVIN T, AND AMYLOID DETECTION METHOD

TECHNICAL FIELD

The present invention relates to a method for purifying pure thioflavin T. The present invention also relates to a method for producing pure thioflavin T, a composition containing thioflavin T, and a method for detecting amyloid.

BACKGROUND ART

Thioflavin T (ThT) is the most famous material known as a fluorescent staining pigment for amyloid, which is a special protein aggregate, and it is used for various studies.

It is known that two kinds of fluorescence are observed from a commercially available ThT reagent. Those two kinds of fluorescence are fluorescence having a peak wavelength near 440 nm (excitation wavelength is 350 nm, for example), and fluorescence having a peak wavelength near 480 nm (excitation wavelength is 430 nm, for example). It remains still unclear whether the fluorescence at the short wavelength side (fluorescence having a peak wavelength near 440 nm) originates from ThT or impurities in a ThT reagent.

For example, according to early studies, it has been reported in Non Patent Literature 1 that the impurities in a ThT reagent have an absorption for a wavelength of 350 nm and they are dissolved in hexane or cyclohexane. Meanwhile, according to Non Patent Literature 2, as the fluorescence of a wavelength 445 nm remains even after repetition of ThT purification (recrystallization), it is concluded as fluorescence originating from ThT and categorized as fluorescence which is emitted from part of a functional group forming ThT (local fluorescence). This local fluorescence hypothesis is supported by Non Patent Literature 3, and the physical and chemical origin of the hypothesis is discussed in the same document. Meanwhile, it is reported in Non Patent Literature 4 that ThT causes a photoreaction upon light illumination, and, by having an absorption band near a wavelength of 350 nm, it produces a photoreaction product which emits fluorescence with a wavelength of 450 nm, and it is described that the impurities in a ThT reagent originate from a photoreaction product of ThT.

CITATION LIST

Patent Literature

Non Patent Literature 1: J. Appl. Spectrosc., 2003, Vol. 70, No. 6, pp. 868-874
Non Patent Literature 2: S. Chem. Biol., 2010, Vol. 3, pp. 1-18
Non Patent Literature 3: Dyes Pigments, 2014, Vol. 110, pp. 97-105
Non Patent Literature 4: J. Phys. Chem. B, 2013, Vol. 117, pp. 3459-3468

SUMMARY OF INVENTION

Problems to be Solved by the Invention

The reason why it remains still unclear whether the fluorescence at the short wavelength side (fluorescence having a peak wavelength near 440 nm) originates from ThT or impurities in a ThT reagent is that, according to a technique of a related art, a ThT reagent having no fluorescence at the short wavelength side (pure ThT) cannot be obtained.

In consideration of the technical background which is described above, an object of the present invention is to provide a method for obtaining a ThT reagent having no fluorescence at the short wavelength side, that is, a method for obtaining pure ThT.

Means for Solving the Problems

The present invention relates to a method for purifying pure thioflavin T, including a step of preparing a thioflavin T solution in which crude thioflavin T is dissolved in a polar solvent, a step of bringing the thioflavin T solution into contact with a non-polar polymeric porous body, and a step of separating the thioflavin T solution after the contact from the non-polar polymeric porous body.

Because the method according to the present invention is to bring thioflavin T into contact with a non-polar polymeric porous body after the thioflavin T is prepared as a solution of a polar solvent, a ThT reagent having no fluorescence at the short wavelength side (pure ThT) can be obtained. This also means that the fluorescence at the short wavelength side is not the fluorescence originating from ThT but the fluorescence originating from fluorescent impurities. Furthermore, according to studies conducted by the inventors of the present invention, it also becomes evident that the fluorescent impurities are produced again when ThT having no fluorescence at the short wavelength side is exposed to light (in particular, light with wavelength of 475 nm or lower). Namely, it is believed that the fluorescent impurities are a photoreaction product of ThT.

In the present specification, the "crude thioflavin T (crude ThT)" means a mixture of the aforementioned fluorescent impurities and ThT. Those conventionally referred to as "ThT" correspond to crude ThT of the present specification as they all include the fluorescent impurities that are described above.

In the present specification, the "pure thioflavin T (pure ThT)" means a ThT reagent having no fluorescence at the short wavelength side, and the "ThT reagent" has the same meaning as a molecular assembly containing ThT (composition). Thus, the "pure ThT" can be also recognized as a molecular assembly of ThT which includes substantially no fluorescent impurities or a molecular assembly which substantially consists of ThT. It is preferable that the "pure ThT" is a molecular assembly of ThT which includes no fluorescent impurities or a molecular assembly which consists of ThT.

Regarding the method described above, it is preferable that the step of bringing the thioflavin T solution into contact with a non-polar polymeric porous body and the step of separating the thioflavin T solution after the contact from the non-polar polymeric porous body are carried out in a state in which light with a wavelength of 475 nm or lower is blocked. Accordingly, production of a new photoreaction product (fluorescent impurities) can be suppressed more, and thus pure ThT can be purified with even higher efficiency.

It is also possible that the method further includes a step of measuring light emission intensity of the fluorescence of a separated thioflavin T solution which has a peak wavelength near 440 nm and determining whether or not the measured light emission intensity reaches the background level, in which when it is determined in the step of determination that the measured light emission intensity does not reach the background level, a step of bringing the thioflavin T solution into contact with a non-polar polymeric porous body; and a step of separating the thioflavin T solution after the contact from the non-polar polymeric porous body are further carried out for the thioflavin T solution. Accordingly, it is possible to have a progress of the purification while monitoring the fluorescence originating from the fluorescent impurities.

The polar solvent may be a solvent selected from the group consisting of an aqueous solvent, methanol, ethanol, acetonitrile, and dimethyl sulfoxide, and a mixture solvent in which two or more types thereof are mixed with each other.

The non-polar polymeric porous body is preferably a porous structural body which is formed of a polymer selected from the group consisting of polyvinylidene fluoride (PVDF), polysulfone, polyether sulfone, nylon, cellulose acetate, and nitrocellulose, and two or more types thereof. By using the porous structural body, pure ThT can be purified with even higher efficiency.

The aforementioned method is preferably a method in which the non-polar polymeric porous body is a non-polar polymer membrane, and the step of bringing the thioflavin T solution into contact with a non-polar polymeric porous body; and the step of separating the thioflavin T solution after the contact from the non-polar polymeric porous body are carried out by filtration of a thioflavin T solution with the aforementioned non-polar polymer membrane. By carrying out the purification based on a filtration operation, pure ThT can be purified conveniently and quickly.

The present invention further provides a method for producing pure thioflavin T including a purification process for carrying out the above method for purifying pure thioflavin T.

The present invention further provides a composition containing thioflavin T in which light emission intensity of the fluorescence having a peak wavelength near 440 nm is at the background level.

Because the composition according to the present invention is a ThT-containing composition in which fluorescent impurities are not included, when it is used for fluorescent staining of amyloid, for example, the influence of the fluorescent impurities can be excluded so that the test results and diagnosis results can be obtained at higher precision. As such, the composition of the present invention is suitable for use in detecting amyloid.

The present invention still further provides a method for detecting amyloid, including a step of bringing a test sample into contact with a fluorescent reagent containing thioflavin T and a step of detecting fluorescence of the thioflavin T, in which the fluorescent reagent is the composition described above.

According to the method for detecting amyloid of the present invention, amyloid can be detected with higher precision from the viewpoint that the method uses a ThT-containing composition in which fluorescent impurities are not included.

The amyloid may be amyloid β. It is known that amyloid β is accumulated in a brain of a patient with Alzheimer's disease (senile plaque). Detection of amyloid β with high precision may greatly contribute to the elucidation of symptoms associated with Alzheimer's disease or the like.

The purification method according to the present invention is based on a novel finding that fluorescent impurities can be removed by bringing a thioflavin T solution into contact with a non-polar polymeric porous body. Namely, it can be recognized as an invention in which a non-polar polymeric porous body is employed for new use of removing fluorescent impurities from crude thioflavin T. As such, the present invention also provides an impurity removing agent for removing fluorescent impurities from crude thioflavin T in which the impurity removing agent is formed of a non-polar polymeric porous body. The present invention can be also recognized as a use or an application of a non-polar polymeric porous body for removing fluorescent impurities from crude thioflavin T.

Effects of the Invention

According to the present invention, it is possible to obtain pure ThT which cannot be obtained by a technique of a related art.

ThT is a fluorescent staining reagent which is the first choice for amyloid staining, and it is used not only for a study of amyloid but also for a pathological diagnosis of a disease related with amyloid. By using pure ThT for amyloid staining, the influence of fluorescent impurities on measurement results can be excluded, and thus test results and diagnosis results can be obtained with higher precision.

EMBODIMENTS FOR CARRYING OUT THE INVENTION

Figure 1:
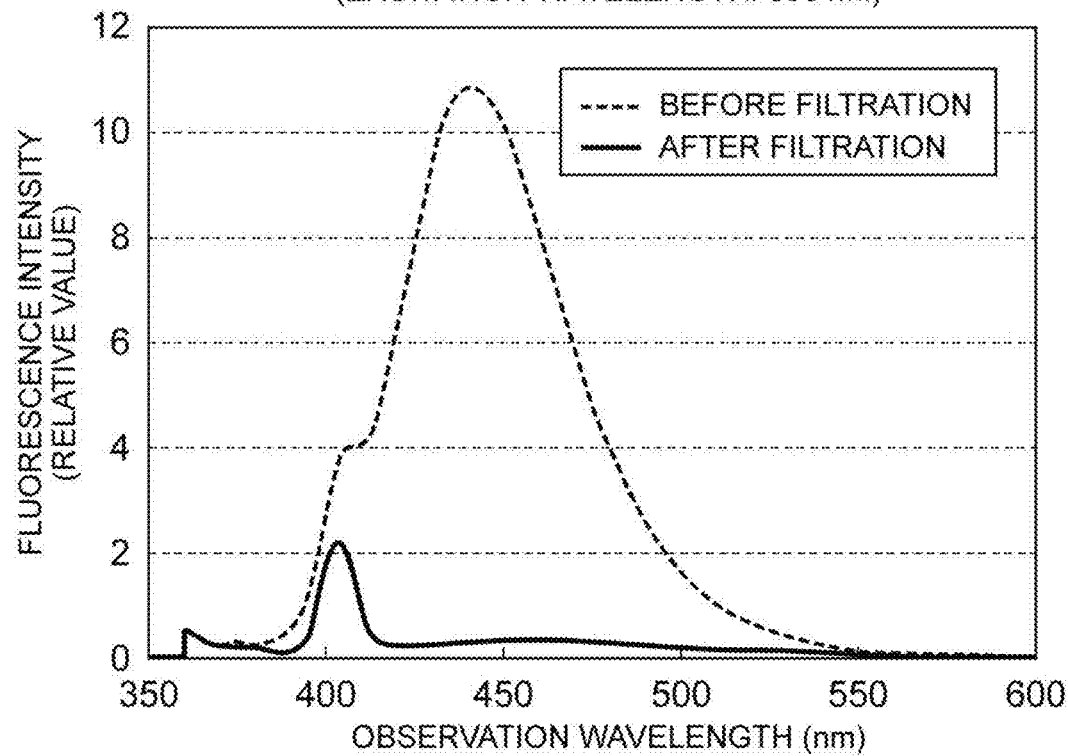
FIG. 1(A) is a drawing comparing the fluorescence spectrum before and after the purification in Example 1 (excitation wavelength: 350 nm)
FIG. 1(B) is a drawing comparing the excitation spectrum before and after the purification in Example 1 (observation wavelength: 440 nm). The non-polar polymeric porous body is a filtration membrane formed of PVDF.
Figure 1:
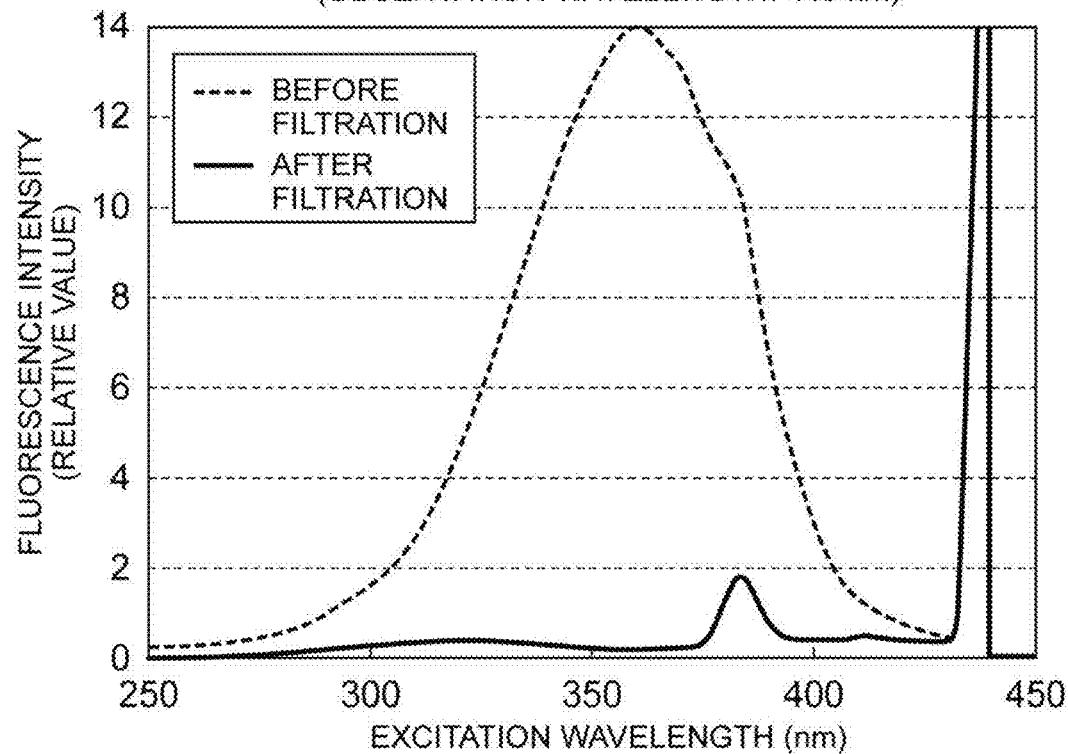

Hereinbelow, embodiments for carrying out the present invention are described in detail. However, the present invention is not limited to the embodiments that are given below.

[Thioflavin T]

Thioflavin T (ThT) is represented by the following chemical formula, and it is a known chemical compound also referred to as 4-(3,6-dimethyl-1,3-benzothiazol-3-ium-2-yl)-N,N-dimethylaniline chloride.

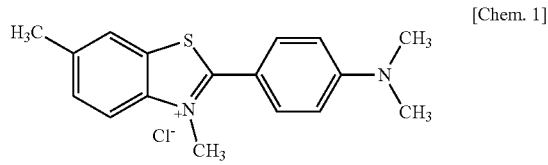

[Chem. 1]

ThT exhibits fluorescence having a peak wavelength near 480 nm (excitation wavelength is 430 nm, for example). Meanwhile, upon illumination of light, ThT generates a photoreaction product (fluorescent impurities) which exhibits fluorescence having a peak wavelength near 440 nm (excitation wavelength is 350 nm, for example). Until now, it remains impossible to separate ThT from a mixture (crude ThT) of the fluorescent impurities and ThT.

The method for obtaining crude ThT is not particularly limited. It is possible to obtain it by purchasing a commercially available ThT reagent, or by synthesizing it according to a known method, for example.

[Method for Purifying Thioflavin T]

The method for purifying thioflavin T according to this embodiment includes a step of preparing a thioflavin T solution in which crude thioflavin T is dissolved in a polar solvent (preparation step), a step of bringing the thioflavin T solution into contact with a non-polar polymeric porous body (contact step), and a step of separating the thioflavin T solution after the contact from the non-polar polymeric porous body (separation step). Furthermore, it is also possible to further include a step of measuring light emission intensity of the fluorescence of a separated thioflavin T solution which has a peak wavelength near 440 nm and determining whether or not the measured light emission intensity reaches the background level (determination step). According to the purification method of this embodiment, pure ThT can be obtained.

In the preparation step, a thioflavin T solution in which crude thioflavin T is dissolved in a polar solvent is prepared. The ThT solution can be prepared by dissolving crude ThT in a polar solvent. Furthermore, when ThT is prepared as a solution in which it is dissolved in a polar solvent as it is synthesized or the like, the solution can be taken as a ThT solution.

As for the polar solvent, a solvent in which ThT can be dissolved can be used without any particular limitation. As for the polar solvent, a solvent with relative permittivity of 10 or more can be used, for example. Specific examples of the polar solvent include an aqueous solvent, methanol, ethanol, acetonitrile, dimethyl sulfoxide, and a mixture solvent in which two or more types thereof are mixed with each other. Examples of the aqueous solvent include water (including purified water used for pharmaceutical products, ion exchange water prepared by ion exchange, ultrafiltration, or the like, and ultra-pure water), a buffer solution like phosphate buffered physiological saline (PBS) and Tris-buffered physiological saline (TBS), and physiological saline. The polar solvent to be used is suitably selected depending on the use of ThT after the purification. For example, when ThT after the purification is used for detection of amyloid, an aqueous solvent is preferable as a polar solvent.

ThT concentration in the ThT solution is not particularly limited. However, it is generally within a range of 0.001 to 10 mmol/L. From the viewpoint of further suppressing new generation of a photoreaction product (fluorescent impurities) during the purification process, it is preferable to have low ThT concentration. For example, ThT concentration is preferably within a range of 0.01 to 7.5 mmol/L. It is more preferably within a range of 0.1 to 5 mmol/L, and even more preferably within a range of 0.5 to 2 mmol/L. Furthermore, ThT concentration in the ThT solution can be set, depending on the use of ThT after the purification, such that it is not necessary to carry out again the dilution or concentration.

In the contact step, the ThT solution is brought into contact with a non-polar polymeric porous body. In the separation step, the ThT solution after contact with a non-polar polymeric porous body is separated from the non-polar polymeric porous body.

The non-polar polymeric porous body is a porous structural body formed of a non-polar polymer.

As for the non-polar polymer, a polymer with relative permittivity of less than 10 can be used (for example, organic polymer and inorganic polymer). Specific examples of the non-polar polymer include regenerated cellulose (relative permittivity: 3.2 to 7.5), polyvinylidene fluoride (PVDF, relative permittivity: 8.4), polytetrafluoroethylene (relative permittivity: 2.1), cellulose acetate (relative permittivity: 3.2 to 7.0), nitrocellulose (relative permittivity: 6.2 to 7.5), polyethylene (relative permittivity: 2.2 to 2.4), polypropylene (relative permittivity: 1.5 to 1.8), polysulfone (relative permittivity: 3.0 to 3.1), polyether sulfone (relative permittivity: 3.8), polycarbonate (relative permittivity: 2.9 to 3.0), nylon (relative permittivity: 4.0 to 5.0), an acryl polymer (polymer or copolymer of acrylic acid, methacrylic acid, or a derivative thereof (for example, ester like methyl acrylate and methyl methacrylate), relative permittivity: 2.7 to 4.5), glass fiber (relative permittivity: 3.7 to 7.0), and a mixture of 2 or more kinds thereof. As for the non-polar polymer, polyvinylidene fluoride, polytetrafluoroethylene, cellulose acetate, nitrocellulose, polysulfone, polyether sulfone, nylon, and a mixture of 2 or more kinds thereof are preferable. Polyvinylidene fluoride, polysulfone, polyether sulfone, nylon, and a mixture of cellulose acetate and nitrocellulose are more preferable.

The porous structural body is a structural body having fine pores formed therein, and specific examples thereof include a membrane (film), a sheet, a particulate body, and a foamed body.

The non-polar polymeric porous body can be produced by a common method like phase separation method, extraction method, stretching method, track etching method, and calcination method.

Examples of the non-polar polymeric porous body include a non-polar polymeric membrane (filtration membrane) and a non-polar polymeric particulate body. As for the non-polar polymeric porous body, a commercially available product may be used, and examples thereof include a polyvinylidene fluoride filtration membrane (for example, membrane filter Millex-GV (manufactured by Merck Millipore)), a filtration membrane of a mixture of cellulose acetate and nitrocellulose (for example, membrane filter Vented-Millex-GS (manufactured by Merck Millipore)), a cellulose acetate membrane filter (for example, syringe filter ASFIL (manufactured by As One Corporation)), a nylon filtration membrane (for example, syringe filter ASFIL (manufactured by As One Corporation)), a polysulfone filtration membrane (for example, filter Ekicro Disc 25 (manufactured by SHIMADZU CORPORATION)), a polyether sulfone filtration membrane (for example, syringe filter ASFIL (manufactured by As One Corporation)), a polytetrafluoroethylene filtration membrane (for example, syringe filter ASFIL (manufactured by As One Corporation)), an acrylic copolymer filtration membrane (for example, filter Ekicro Disc 13 (manufactured by SHIMADZU CORPORATION)), a polypropylene filtration membrane (for example, syringe filter Puradisc 25 (manufactured by GE Healthcare)), a regenerated cellulose filtration membrane (for example, filter Minisart RC15 (manufactured by Minisart)), and a glass fiber filtration membrane (for example, syringe filter GF (manufactured by As One Corporation)).

The method for bringing the ThT solution into contact with a non-polar polymeric porous body is not particularly limited. Specific examples of the method for contact include a method in which a ThT solution is passed through a non-polar polymer membrane by a filtration operation for having a contact (membrane filtration method), a method in which a ThT solution is allowed to flow through a column filled with a particulate body of a non-polar polymer for having a contact (column filtration method), and a method in which a non-polar polymeric porous body with any shape is added to a ThT solution and stirred therein. From the viewpoint that the contact step and separation step can be carried out conveniently and quickly, the membrane filtration method and column filtration method are preferable. The membrane filtration method is more preferable.

The method for separating a ThT solution from a non-polar polymeric porous body is not particularly limited, and any method commonly used for solid-liquid separation can be used.

In the determination step, light emission intensity of the fluorescence of a separated ThT solution which has a peak wavelength near 440 nm is measured and determination is made to see whether or not the measured light emission intensity reaches the background level.

In the determination step, part of the ThT solution separated from a non-polar polymeric porous body is collected to obtain a measurement sample, and fluorescence intensity is measured. For measurement of the fluorescence intensity, a fluorescence spectrophotometer, a fluorescence plate reader, or the like can be used. More specifically, a measurement sample is illuminated with light having a wavelength of 300 to 430 nm, and light emission in a wavelength of 440 to 460 nm (fluorescence) is measured accordingly. The wavelength of light for illumination can be suitably set within the aforementioned range. However, it is preferably a wavelength of 350 nm. The wavelength of fluorescence to be measured can be suitably set within the aforementioned range. However, it is preferably a wavelength of 440 nm.

Subsequently, determination is made to see whether or not the measured light emission intensity reaches the background level. When it is determined that the measured light emission intensity does not reach the background level, the contact step and the separation step are repeated additionally. When it is determined that the measured light emission intensity reaches the background level, the purification is terminated.

The "background level" means that the fluorescence intensity of a purified ThT solution is almost the same as the fluorescence intensity of a pure ThT solution. Determination of the "background level" can be carried out as described below, for example. Namely, in addition to the fluorescence intensity of a purified ThT solution at a wavelength of 440 nm, the fluorescence intensity at a wavelength of 480 nm is also measured, and the fluorescence ratio resulting from dividing the fluorescence intensity at a wavelength of 440 nm by the fluorescence intensity at a wavelength of 480 nm is obtained. When the fluorescence ratio is within a range of 0.4 to 1.0, it can be determined as "background level." Herein, it is preferably determined as "background level" when the fluorescence ratio is within a range of 0.5 to 0.9, and it is more preferably determined as "background level" when the fluorescence ratio is within a range of 0.6 to 0.8. Furthermore, more briefly, when the measurement value of fluorescence intensity which is measured in the determination step does not decrease any further, it can be determined as "background level."

The ThT solution after completion of the purification can be used directly for next use. If necessary, it can be used as ThT powder for next use after removing the polar solvent. It can be also used for next use after ThT powder is dissolved again in any solvent.

The aforementioned purification method is preferably carried out in a state in which light with a wavelength of 475 nm or lower is blocked. Accordingly, production of new fluorescent impurities is suppressed so that the efficiency of the entire purification method can be enhanced more. It is possible that the entire process of the purification method is carried out in a light-blocked state. However, it is also possible that the process after the contact step is carried out in a light-blocked state. The method for blocking light with a wavelength of 475 nm or lower can be suitably selected. Specifically, it is possible to carry out the purification operation under red light or carry out the purification operation in a (complete) light-blocked state.

[Method for Producing Thioflavin T]

The method for producing thioflavin T according to this embodiment includes a purification process for carrying out the method for purifying thioflavin T which has been described in the above. According to the production method of this embodiment, pure ThT can be obtained.

The production method according to this embodiment may also include, before the purification process, a synthesis process for synthesizing ThT, a dissolution process for dissolving crude ThT in a polar solvent, or the like. It is also possible that a packaging process for packaging the obtained pure ThT is included after the purification process. The packaging process may be a process in which the ThT solution is filled in a container like light-proof bottle (such as brown bottle), for example.

[Composition Containing Thioflavin T]

The composition containing thioflavin T according to this embodiment is a composition in which the light emission intensity of the fluorescence having a peak wavelength near 440 nm is at the background level. Namely, it is a composition which includes substantially no fluorescent impurities or a composition substantially consisting of ThT (molecular assembly). The composition according to one embodiment is a composition which contains thioflavin T and, when illuminated with light having a wavelength of 350 nm, has light emission intensity of the fluorescence having a wavelength of 440 nm at the background level.

The composition according to this embodiment can be any one of a liquid phase and a solid phase. From the viewpoint of suppressing generation of the fluorescent impurities, the composition according to this embodiment is preferably filled in a container like light-proof bottle (such as brown bottle).

The composition according to this embodiment can be obtained by the purification method or production method for ThT that are described above.

Because the composition according to this embodiment substantially contains no fluorescent impurities, when it is used for staining of amyloid, the influence of the fluorescent impurities on the measurement results can be excluded so that the test results and diagnosis results with even higher precision can be obtained. Thus, the composition according to this embodiment can be suitably used as a composition for use in detecting amyloid (fluorescent reagent for detecting amyloid).

[Method for Detecting Amyloid]

Amyloid represents a special aggregate of a protein which has a specific β sheet structure. As a protein for forming amyloid, various kinds are present such as insulin, β2 microglobulin, and amyloid β. Accumulation of certain amyloid in a human body may be a cause of a disease. For example, β2 microglobulin is related with dialysis amyloidosis, and amyloid β is related with Alzheimer's disease.

The method for detecting amyloid according to this embodiment can be carried out according to a common method except that the composition according to the present invention is used as a fluorescent reagent.

[Impurity Removing Agent]

The aforementioned non-polar polymeric porous body captures fluorescent impurities when it is brought into contact with a ThT solution in which crude ThT is dissolved in a polar solvent. By utilizing this characteristic, the non-polar polymeric porous body can be suitable for use in removing the fluorescent impurities from crude ThT.

The impurity removing agent according to this embodiment consists of a non-polar polymeric porous body. It is also possible that the impurity removing agent according to this embodiment is provided as a column for removing impurities in which a non-polar polymeric porous body is filled in the column or a filter for removing impurities in which a molded non-polar polymeric porous body is provided in a porous body with membrane shape.

EXAMPLES

Hereinbelow, the present invention is described more specifically based on Examples. However, the present invention is not limited to the following Examples.

Example 1

Example 1 is an example of purifying pure ThT by applying a porous structural body with membrane shape (filtration membrane), which is formed of PVDF, as a non-polar polymeric porous body.

(Preparation of ThT Solution)

By dissolving ThT (ultra pure grade, manufactured by AAT Bioquest Inc., corresponds to the crude ThT in the present specification) in distilled water, 1 mM ThT solution was obtained.

(Filtration Purification of ThT Solution)

2 mL of 1 mM ThT solution was filtered by using a syringe (manufactured by Terumo Corporation) and a membrane filter Millex-GV (material: hydrophilic PVDF, pore size: 0.22 μm, filter diameter: 33 mm, manufactured by Merck Millipore), and the filtered solution was collected.

(Measurement of Fluorescence)

To 10 μL of the obtained filtered solution, 990 μL of distilled water was added for dilution, and the resultant was filled in a micro cell (light path length: 5 mm) The micro cell filled with the sample was installed in a fluorescent spectrophotometer RF-5000 (manufactured by SHIMADZU CORPORATION), and the fluorescence spectrum was measured at an excitation wavelength of 350 nm. Furthermore, the excitation spectrum was also measured at an observation wavelength of 440 nm.

(Evaluation)

The measurement results of the fluorescence spectrum (excitation wavelength: 350 nm) are shown in FIG. 1(A). As it is shown in FIG. 1(A), it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Furthermore, the measurement results of the excitation spectrum (observation wavelength: 440 urn) are shown in FIG. 1(B). As it is shown in FIG. 1(B), it is recognized that, according to the filtration, the fluorescence which has a peak near the wavelength of 350 nm originating from fluorescent impurities is lost. Namely, according to the filtration operation using a filtration membrane formed of PVDF, the fluorescent impurities that are included in crude ThT can be removed.

Example 2

Example 2 is an example of purifying pure ThT by applying a porous structural body with membrane shape (filtration membrane), which is formed of mixed cellulose ester (mixture of cellulose acetate and nitrocellulose: MCE), as a non-polar polymeric porous body. The preparation of a ThT solution and measurement of fluorescence were carried out in the same manner as Example 1.

(Filtration Purification of ThT Solution)

2 mL of 1 mM ThT solution was filtered by using a syringe (manufactured by Terumo Corporation) and a membrane filter Vented-Millex-GS (material: MCE, pore size: 0.22 μm, filter diameter: 25 mm, manufactured by Merck Millipore), and the filtered solution was collected.

(Evaluation)

Figure 2:
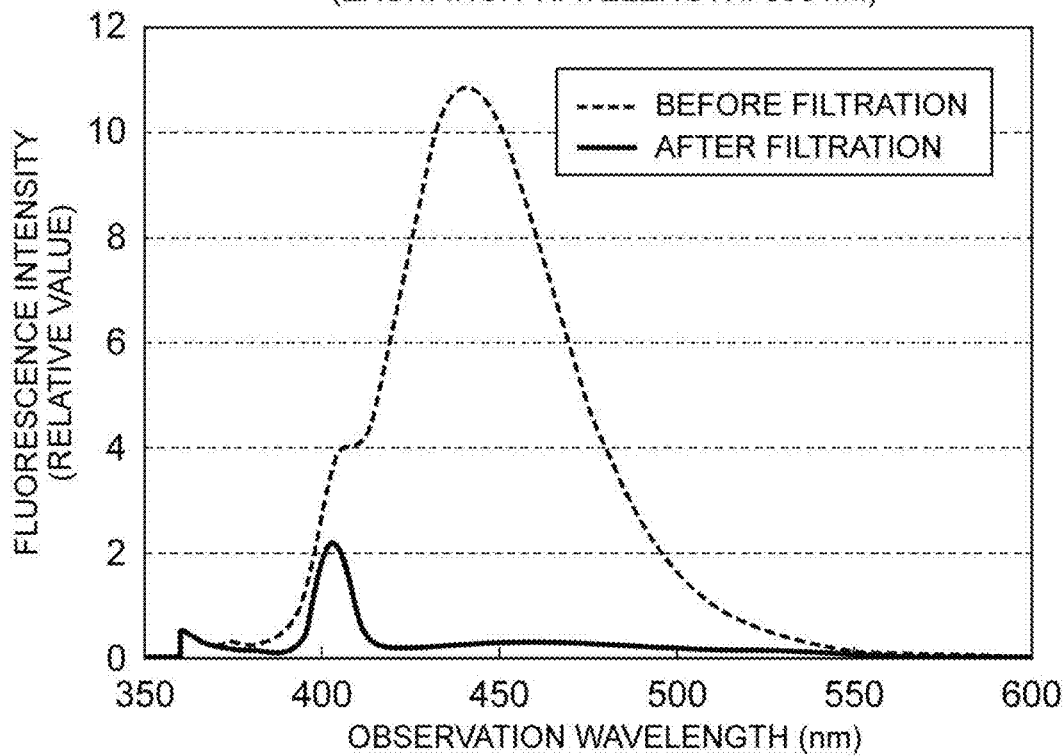
FIG. 2(A) is a drawing comparing the fluorescence spectrum before and after the purification in Example 2 (excitation wavelength: 350 nm).
FIG. 2(B) is a drawing comparing the excitation spectrum before and after the purification in Example 2 (observation wavelength: 440 nm). The non-polar polymeric porous body is a filtration membrane formed of mixed cellulose ester (MCE).
Figure 2:
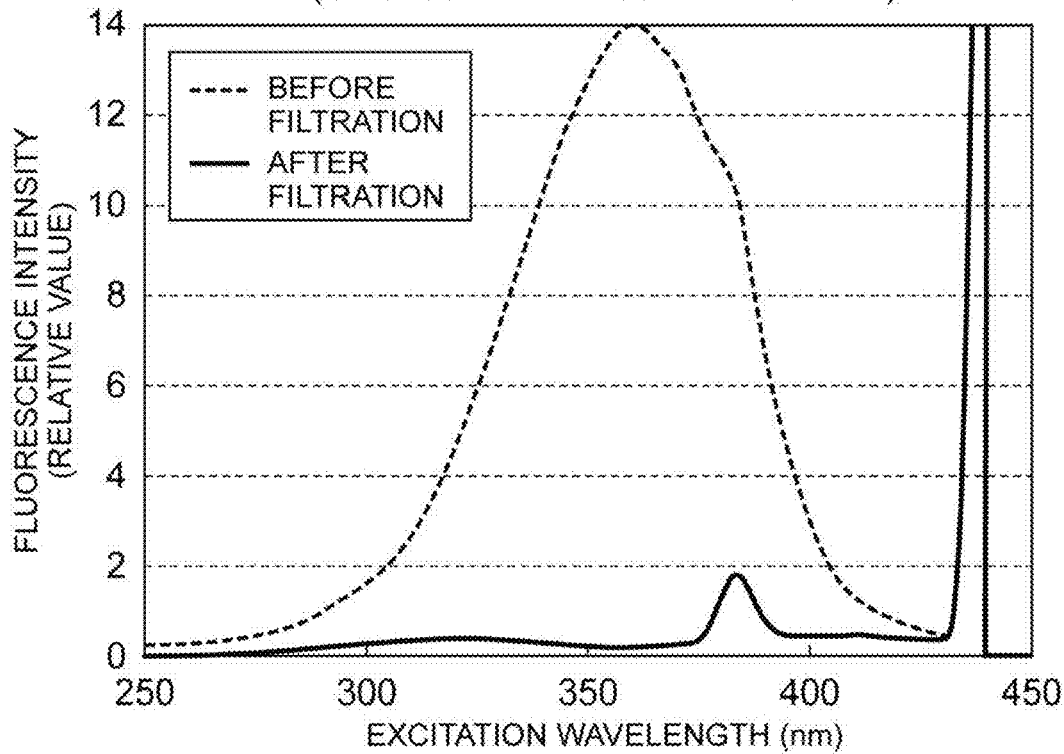

The measurement results of the fluorescence spectrum (excitation wavelength: 350 nm) are shown in FIG. 2(A). As it is shown in FIG. 2(A), it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Furthermore, the measurement results of the excitation spectrum (observation wavelength: 440 nm) are shown in FIG. 2(B). As it is shown in FIG. 2(B), it is recognized that, according to the filtration, the fluorescence which has a peak near the wavelength of 350 nm originating from fluorescent impurities is lost. Namely, according to the filtration operation using a filtration membrane formed of MCE, the fluorescent impurities that are included in crude ThT can be removed.

Example 3

Figure 3:
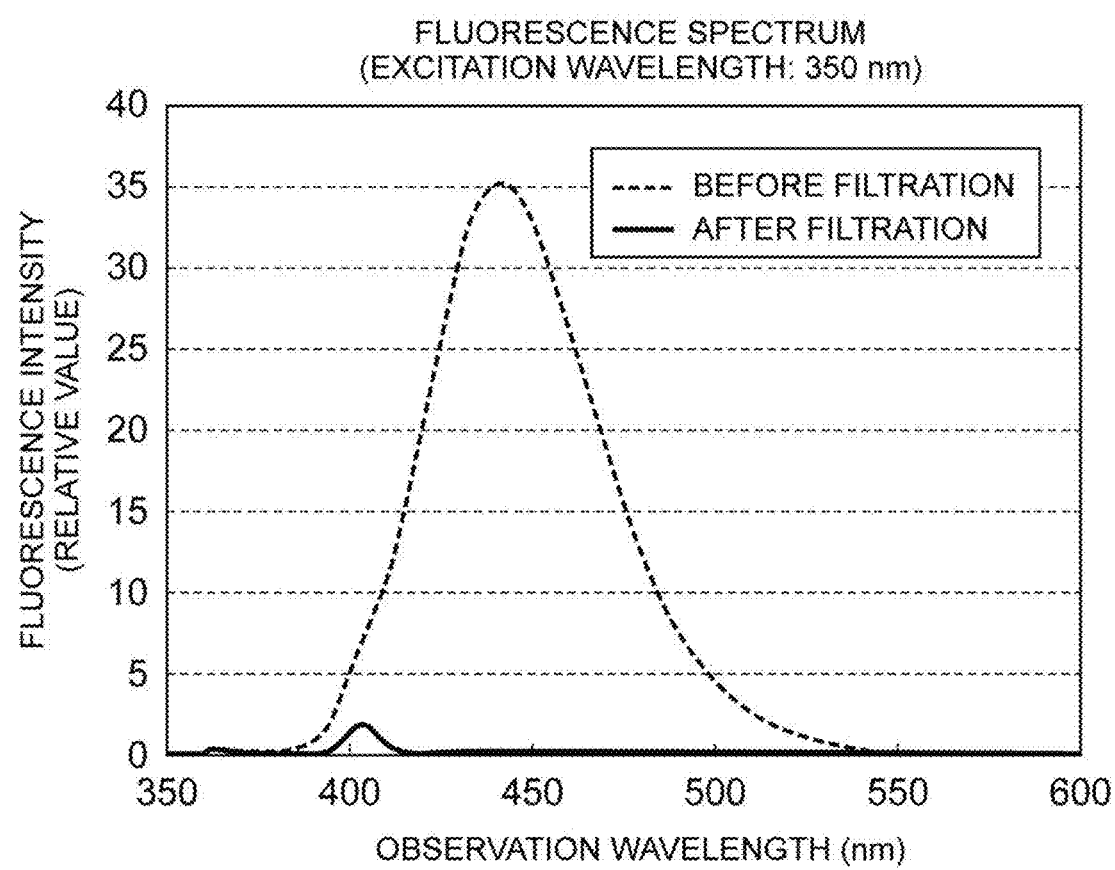
FIG. 3 is a drawing comparing the fluorescence spectrum before and after the purification in Example 3 (excitation wavelength: 350 nm). The non-polar polymeric porous body is a filtration membrane formed of cellulose acetate.

Example 3 is an example of purifying pure ThT by applying a porous structural body with membrane shape (filtration membrane), which is formed of cellulose acetate, as a non-polar polymeric porous body.
(Preparation of ThT Solution)
By dissolving ThT (ultra pure grade, manufactured by AAT Bioquest Inc., corresponds to the crude ThT in the present specification) in distilled water, 10 mM ThT solution was obtained.
(Filtration Purification of ThT Solution)
1 mL of 10 mM ThT solution was filtered by using a syringe (manufactured by Terumo Corporation) and a syringe filter ASFIL (material: cellulose acetate, pore size: 0.45 vim, filter diameter: 25 mm, manufactured by As One Corporation), and the filtered solution was collected.
(Measurement of Fluorescence)
To 2 μL of the obtained filtered solution, 1998 μL of distilled water was added for dilution, and 1000 μL of the diluted solution was filled in a micro cell (light path length: 5 mm). The micro cell filled with the sample was installed in a fluorescent spectrophotometer RF-5000 (manufactured by SHIMADZU CORPORATION), and the fluorescence spectrum was measured at an excitation wavelength of 350 nm.
(Evaluation)
The measurement results of the fluorescence spectrum (excitation wavelength: 350 nm) are shown in FIG. 3. As it is shown in FIG. 3, it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Namely, according to the filtration operation using a filtration membrane formed of cellulose acetate, the fluorescent impurities that are included in crude ThT can be removed.

Example 4

Figure 4:
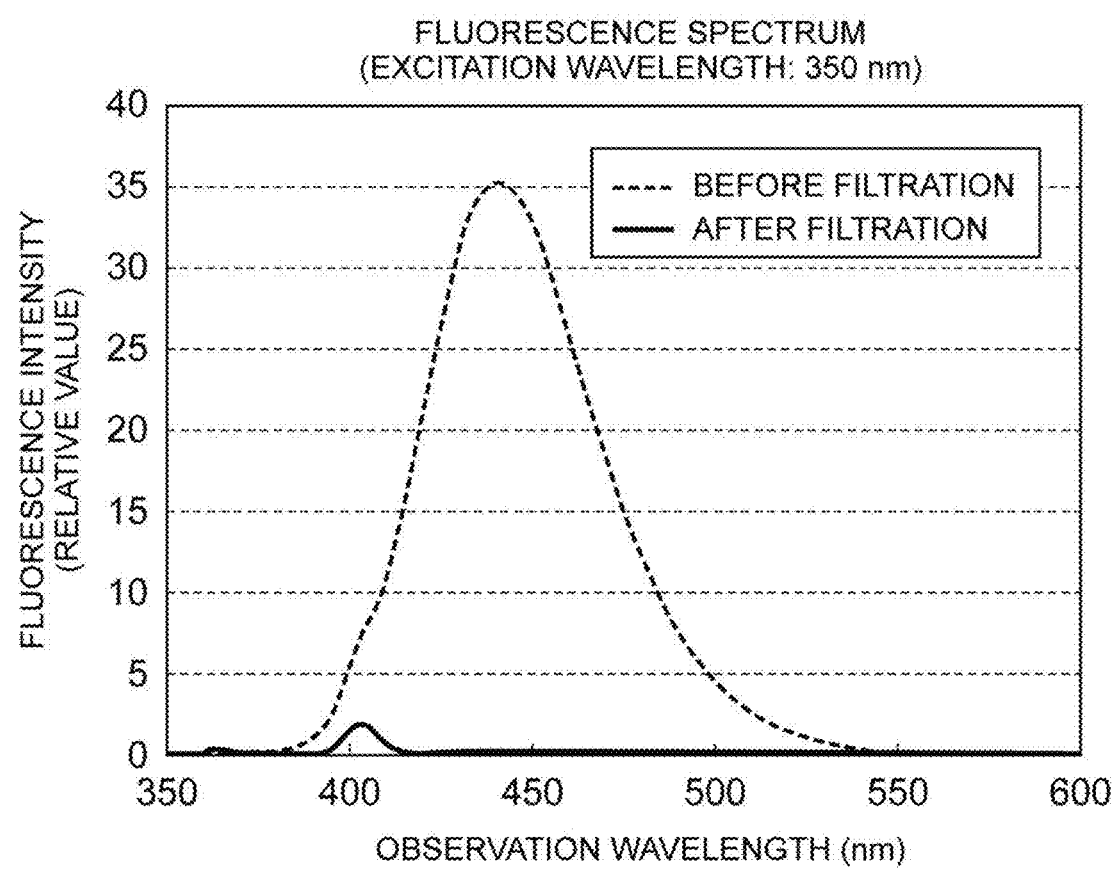
FIG. 4 is a drawing comparing the fluorescence spectrum before and after the purification in Example 4 (excitation wavelength: 350 nm). The non-polar polymeric porous body is a filtration membrane formed of nylon.

Example 4 is an example of purifying pure ThT by applying a porous structural body with membrane shape (filtration membrane), which is formed of nylon, as a non-polar polymeric porous body. The preparation of a ThT solution and measurement of fluorescence were carried out in the same manner as Example 3.
(Filtration Purification of ThT Solution)
1 mL of 10 mM ThT solution was filtered by using a syringe (manufactured by Terumo Corporation) and a syringe filter ASFIL (material: nylon, pore size: 0.45 μm, filter diameter: 25 mm, manufactured by As One Corporation), and the filtered solution was collected.
(Evaluation)
The measurement results of the fluorescence spectrum (excitation wavelength: 350 nm) are shown in FIG. 4. As it is shown in FIG. 4, it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Namely, according to the filtration operation using a filtration membrane formed of nylon, the fluorescent impurities that are included in crude ThT can be removed.

Example 5

Figure 5:
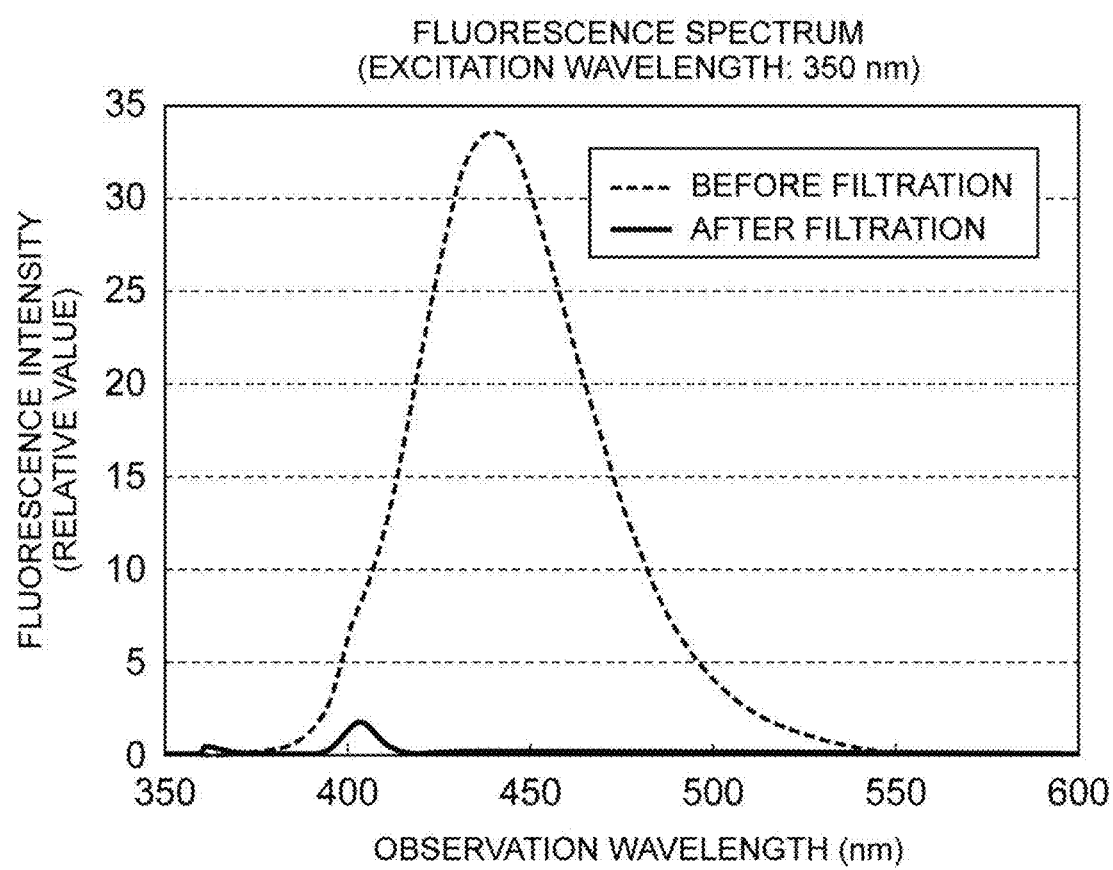
FIG. 5 is a drawing comparing the fluorescence spectrum before and after the purification in Example 5 (excitation wavelength: 350 nm) The non-polar polymeric porous body is a filtration membrane formed of polysulfone.

Example 5 is an example of purifying pure ThT by applying a porous structural body with membrane shape (filtration membrane), which is formed of polysulfone, as a non-polar polymeric porous body. The preparation of a ThT solution and measurement of fluorescence were carried out in the same manner as Example 3.
(Filtration Purification of ThT Solution)
1 mL of 10 mM ThT solution was filtered by using a syringe (manufactured by Terumo Corporation) and a filter Ekicro Disc 25 (material: polysulfone, pore size: 0.2 μm, filter diameter: 25 mm, manufactured by SHIMADZU CORPORATION), and the filtered solution was collected.
(Evaluation)
The measurement results of the fluorescence spectrum (excitation wavelength: 350 nm) are shown in FIG. 5. As it is shown in FIG. 5, it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Namely, according to the filtration operation using a filtration membrane formed of polysulfone, the fluorescent impurities that are included in crude ThT can be removed.

Example 6

Figure 6:
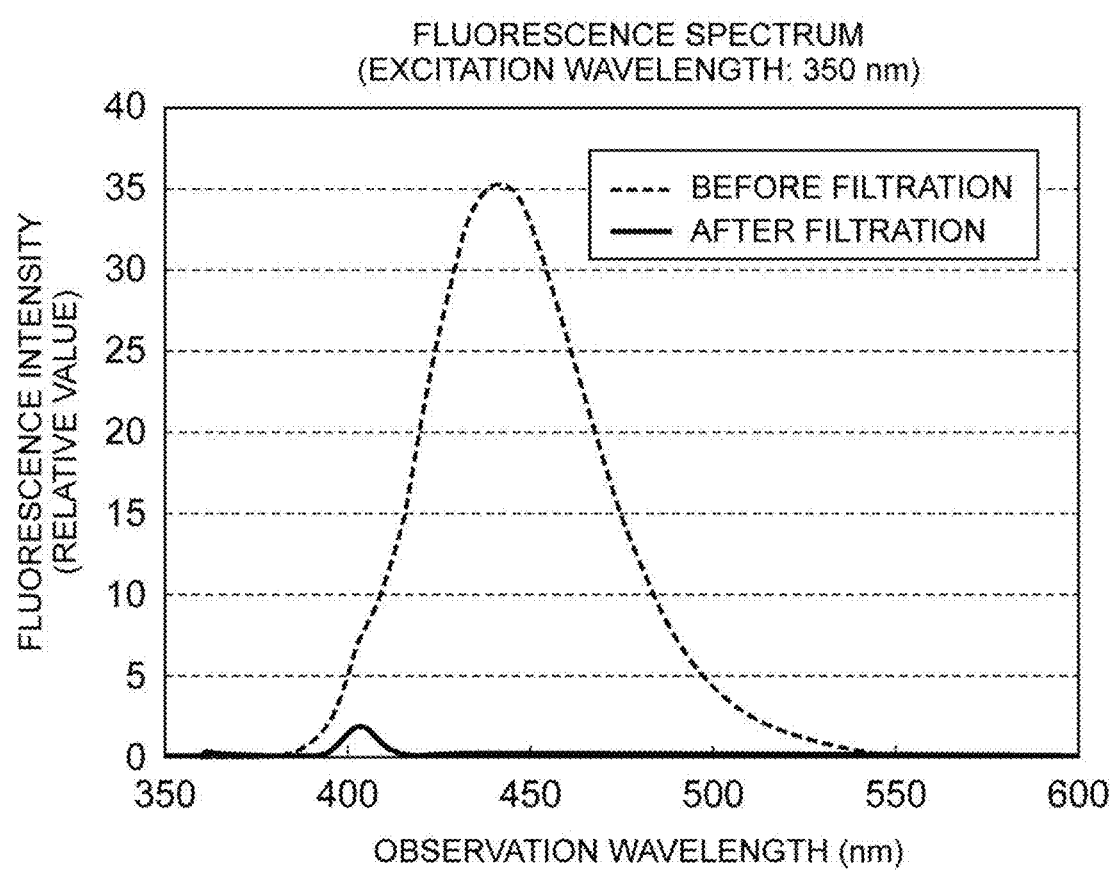
FIG. 6 is a drawing comparing the fluorescence spectrum before and after the purification in Example 6 (excitation wavelength: 350 nm). The non-polar polymeric porous body is a filtration membrane formed of polyether sulfone.

Example 6 is an example of purifying pure ThT by applying a porous structural body with membrane shape (filtration membrane), which is faulted of polyether sulfone, as a non-polar polymeric porous body. The preparation of a ThT solution and measurement of fluorescence were carried out in the same manner as Example 3.
(Filtration Purification of ThT Solution)
1 mL of 10 mM ThT solution was filtered by using a syringe (manufactured by Terumo Corporation) and a syringe filter ASFIL (material: polyether sulfone, pore size: 0.45 μm, filter diameter: 25 mm, manufactured by As One Corporation), and the filtered solution was collected.
(Evaluation)
The measurement results of the fluorescence spectrum (excitation wavelength: 350 nm) are shown in FIG. 6. As it is shown in FIG. 6, it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Namely, according to the filtration operation using a filtration membrane formed of polyether sulfone, the fluorescent impurities that are included in crude ThT can be removed.

Example 7

Example 7 is an example of purifying pure ThT by applying a porous structural body with membrane shape (filtration membrane), which is formed of polytetrafluoroethylene, as a non-polar polymeric porous body.
(Preparation of ThT Solution)
By dissolving ThT (ultra pure grade, manufactured by AAT Bioquest Inc., corresponds to the crude ThT in the present specification) in distilled water, 100 μM ThT solution was obtained.

(Filtration Purification of ThT Solution)

2 mL of 100 μM ThT solution was filtered by using a syringe (manufactured by Terumo Corporation) and a syringe filter ASFIL (material: hydrophilic polytetrafluoroethylene, pore size: 0.45 μm, filter diameter: 25 mm, manufactured by As One Corporation), and the filtered solution was collected.

(Measurement of Fluorescence)

To 100 μL of the obtained filtered solution, 9000 μL of distilled water was added for dilution, and 10000 μL of the diluted solution was filled in a micro cell (light path length: 5 mm). The micro cell filled with the sample was installed in a fluorescent spectrophotometer RF-5000 (manufactured by SHIMADZU CORPORATION), and the fluorescence spectrum was measured at an excitation wavelength of 350 nm.

(Evaluation)

Figure 7:
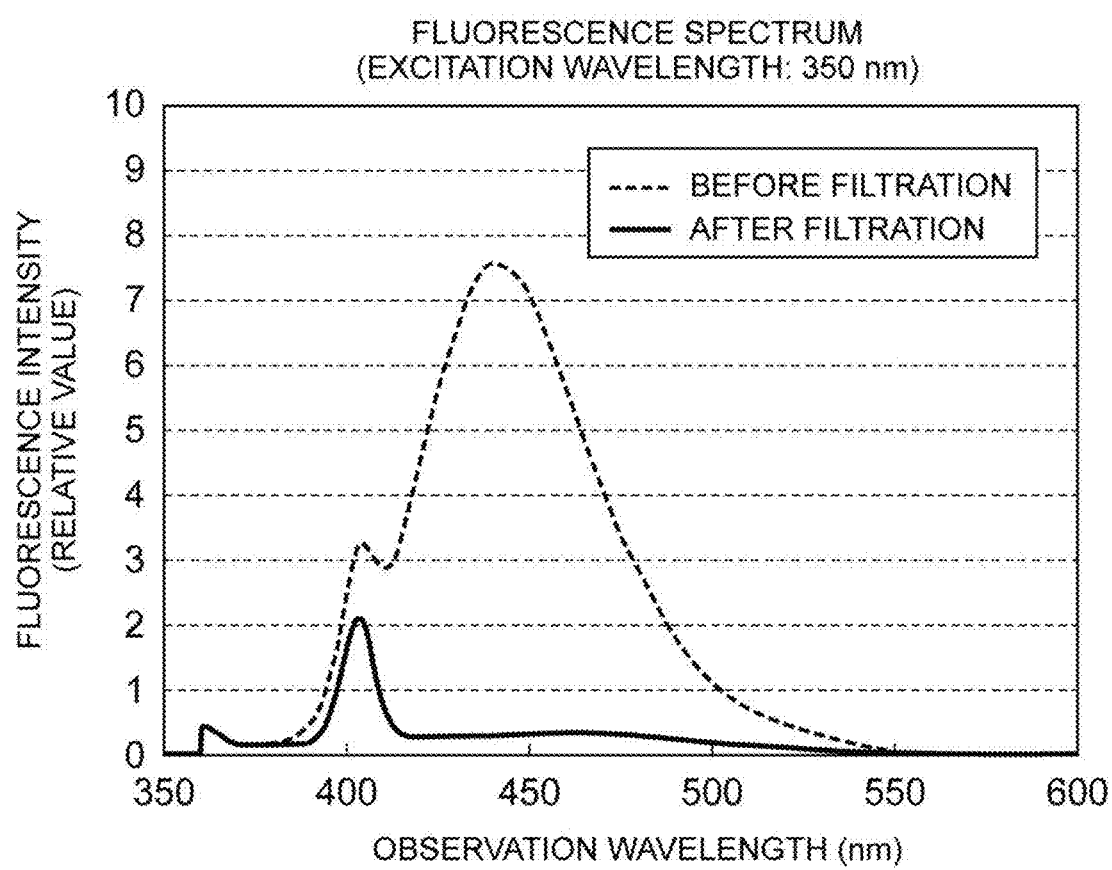
FIG. 7 is a drawing comparing the fluorescence spectrum before and after the purification in Example 7 (excitation wavelength: 350 nm). The non-polar polymeric porous body is a filtration membrane formed of polytetrafluoroethylene.

The measurement results of the fluorescence spectrum (excitation wavelength: 350 nm) are shown in FIG. 7. As it is shown in FIG. 7, it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Namely, according to the filtration operation using a filtration membrane formed of polytetrafluoroethylene, the fluorescent impurities that are included in crude ThT can be removed.

Example 8

Example 8 is an example of purifying pure ThT by applying a porous structural body with membrane shape (filtration membrane), which is formed of an acrylic copolymer, as a non-polar polymeric porous body. The preparation of a ThT solution and measurement of fluorescence were carried out in the same manner as Example 3.

(Filtration Purification of ThT Solution)

0.25 mL of 10 mM ThT solution was filtered by using a syringe (manufactured by Terumo Corporation) and a filter Ekicro Disc 13 (material: acrylic copolymer, pore size: 0.2 μm, filter diameter: 13 mm, manufactured by SHIMADZU CORPORATION), and the filtered solution was collected.

(Evaluation)

Figure 8:
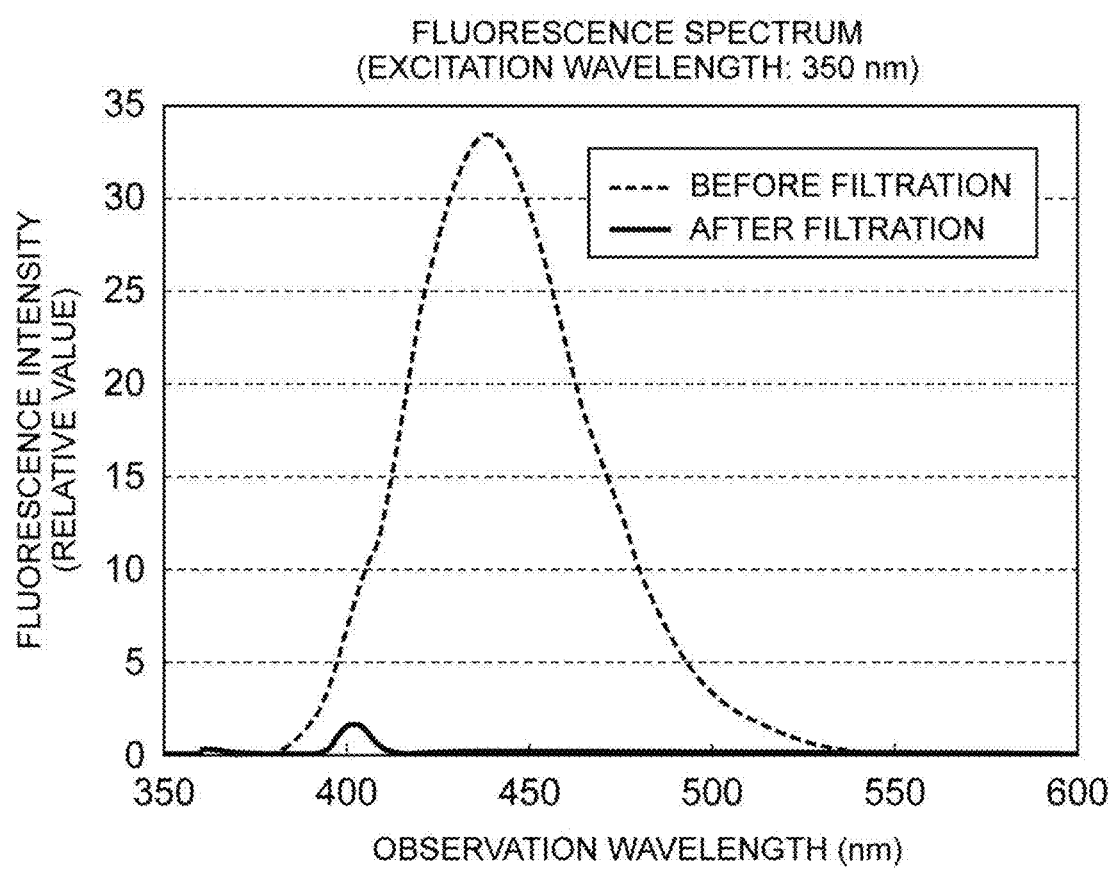
FIG. 8 is a drawing comparing the fluorescence spectrum before and after the purification in Example 8 (excitation wavelength: 350 nm). The non-polar polymeric porous body is a filtration membrane formed of an acrylic copolymer.

The measurement results of the fluorescence spectrum (excitation wavelength: 350 nm) are shown in FIG. 8. As it is shown in FIG. 8, it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Namely, according to the filtration operation using a filtration membrane formed of an acrylic copolymer, the fluorescent impurities that are included in crude ThT can be removed.

Example 9

Example 9 is an example of purifying pure ThT by applying a porous structural body with membrane shape (filtration membrane), which is formed of polypropylene, as a non-polar polymeric porous body. The preparation of a ThT solution and measurement of fluorescence were carried out in the same manner as Example 7.

(Filtration Purification of ThT Solution)

1 mL of 100 μM ThT solution was filtered by using a syringe (manufactured by Terumo Corporation) and a syringe filter Puradisc 25 (material: polypropylene, pore size: 0.45 μm, filter diameter: 25 mm, manufactured by GE Healthcare), and the filtered solution was collected.

(Evaluation)

Figure 9:
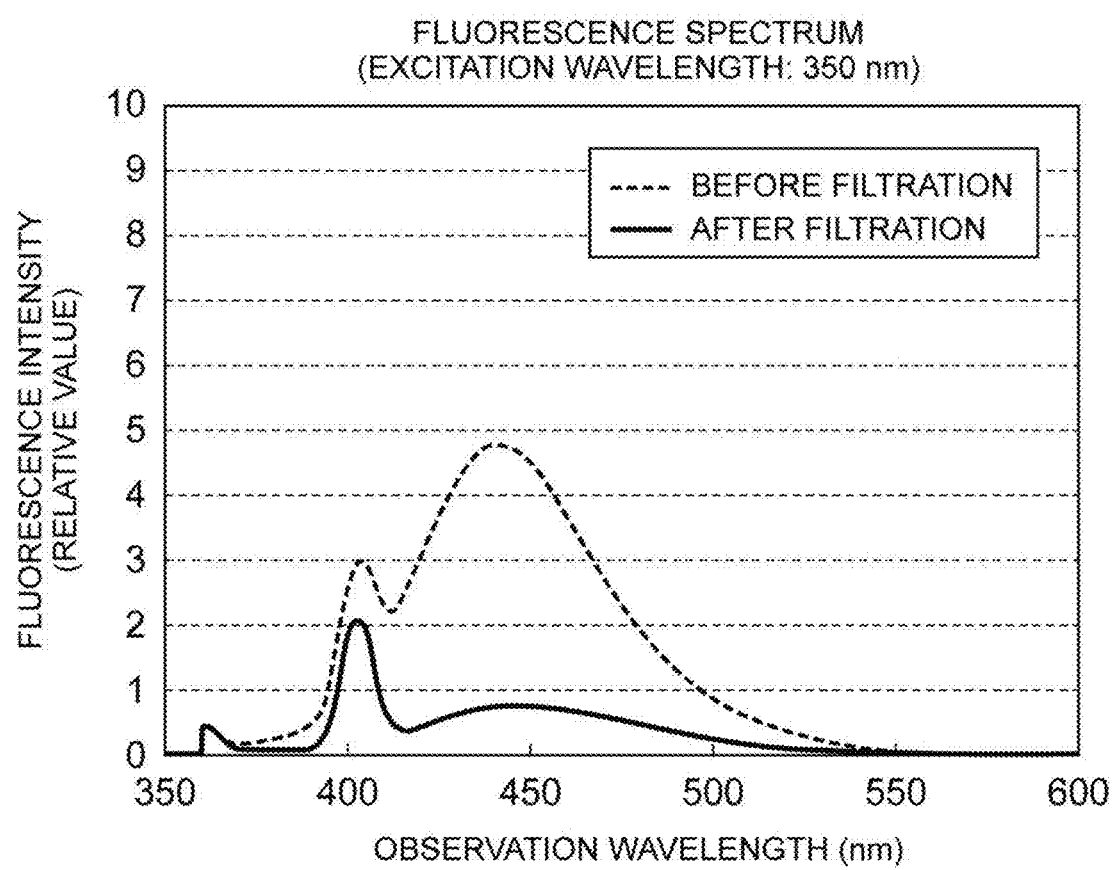
FIG. 9 is a drawing comparing the fluorescence spectrum before and after the purification in Example 9 (excitation wavelength: 350 nm). The non-polar polymeric porous body is a filtration membrane Ruined of polypropylene.

The measurement results of the fluorescence spectrum (excitation wavelength: 350 nm) are shown in FIG. 9. As it is shown in FIG. 9, it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Namely, according to the filtration operation using a filtration membrane formed of polypropylene, the fluorescent impurities that are included in crude ThT can be removed.

Example 10

Example 10 is an example of purifying pure ThT by applying a porous structural body with membrane shape (filtration membrane), which is formed of regenerated cellulose, as a non-polar polymeric porous body. The preparation of a ThT solution and measurement of fluorescence were carried out in the same manner as Example 7.

(Filtration Purification of ThT Solution)

1 mL of 100 μM ThT solution was filtered by using a syringe (manufactured by Terumo Corporation) and a filter Minisart RC15 (material: regenerated cellulose, pore size: 0.2 μm, filter diameter: 15 mm, manufactured by Minisart), and the filtered solution was collected.

(Evaluation)

Figure 10:
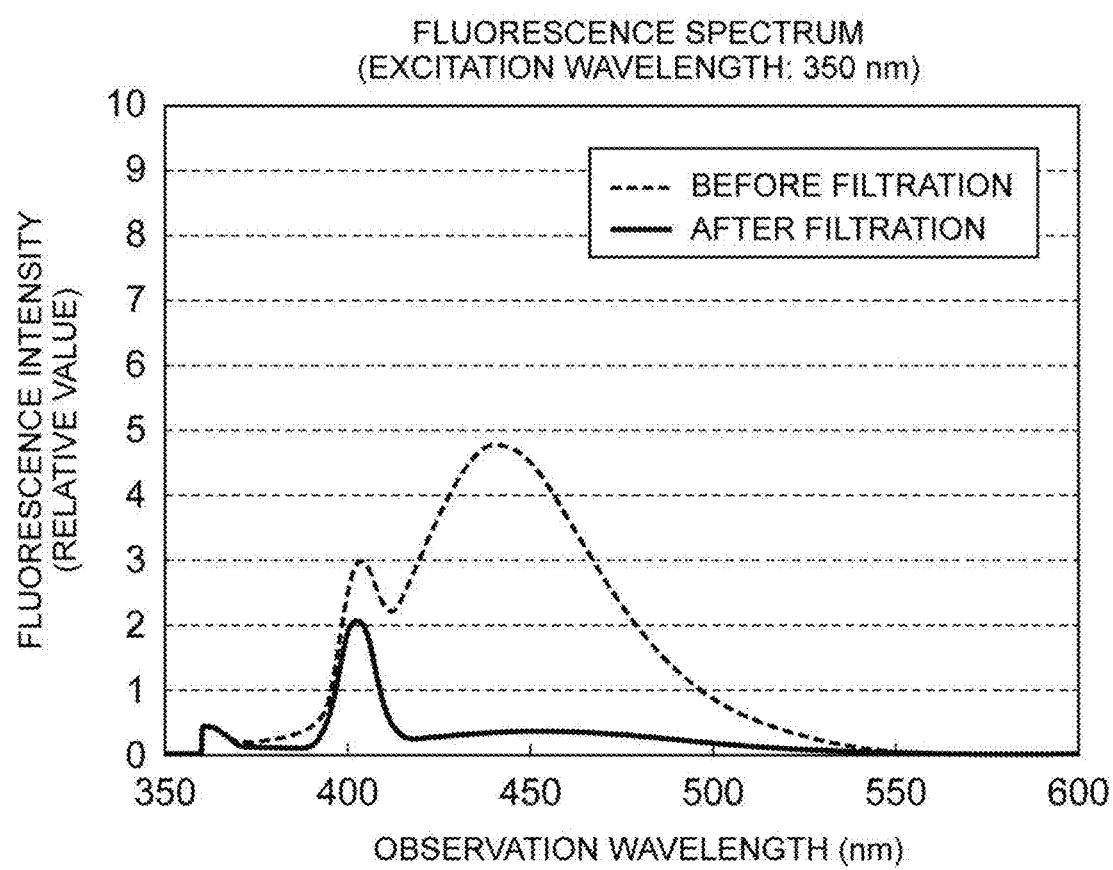
FIG. 10 is a drawing comparing the fluorescence spectrum before and after the purification in Example 10 (excitation wavelength: 350 nm). The non-polar polymeric porous body is a filtration membrane formed of regenerated cellulose.

The measurement results of the fluorescence spectrum (excitation wavelength: 350 nm) are shown in FIG. 10. As it is shown in FIG. 10, it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Namely, according to the filtration operation using a filtration membrane formed of regenerated cellulose, the fluorescent impurities that are included in crude ThT can be removed.

Example 11

Example 11 is an example of purifying pure ThT by applying a porous structural body with membrane shape (filtration membrane), which is formed of glass fiber, as a non-polar polymeric porous body. The preparation of a ThT solution and measurement of fluorescence were carried out in the same manner as Example 7.

(Filtration Purification of ThT Solution)

1 mL of 100 μM ThT solution was filtered by using a syringe (manufactured by Terumo Corporation) and a syringe filter GF (material: glass fiber, pore size: 1.0 μm, filter diameter: 25 mm, manufactured by As One Corporation), and the filtered solution was collected.

(Evaluation)

Figure 11:
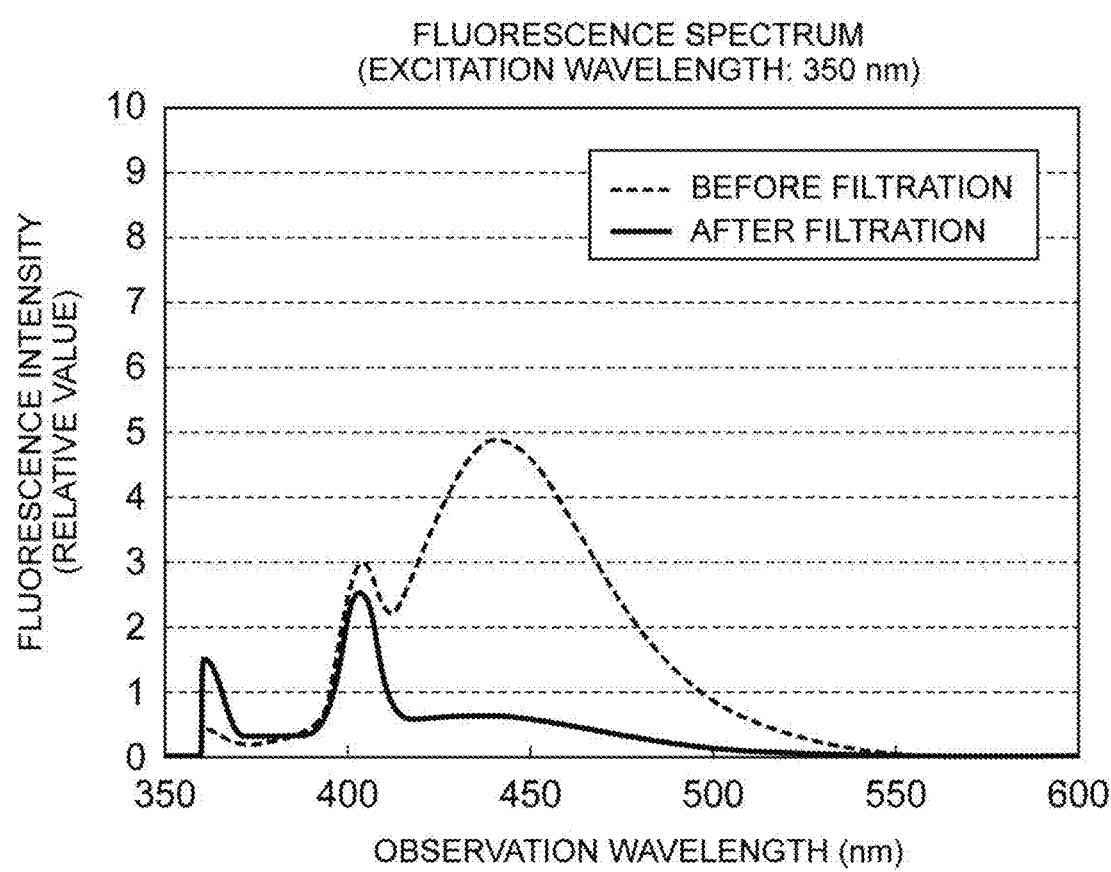
FIG. 11 is a drawing comparing the fluorescence spectrum before and after the purification in Example 11 (excitation wavelength: 350 nm). The non-polar polymeric porous body is a filtration membrane formed of glass fiber.

The measurement results of the fluorescence spectrum (excitation wavelength: 350 nm) are shown in FIG. 11. As it is shown in FIG. 11, it is found that, according to the filtration, the fluorescence which has a peak near the wavelength of 440 nm originating from fluorescent impurities is lost so that the fluorescence which has a peak near the wavelength of 480 nm as the fluorescence intrinsic to ThT remains only. Namely, according to the filtration operation using a filtration membrane formed of glass fiber, the fluorescent impurities that are included in crude ThT can be removed.

The invention claimed is:

1. A method for purifying pure thioflavin T, comprising:
a step of preparing a thioflavin T solution in which crude thioflavin T is dissolved in a polar solvent;
a step of bringing the thioflavin T solution into contact with a non-polar polymeric porous body, thereby removing fluorescent impurities from the thioflavin T solution;
a step of separating the thioflavin T solution, in which the fluorescent impurities were removed, from the non-polar polymeric porous body after the contact in order to generate pure thioflavin T, and
a step of measuring fluorescence intensity of the separated thioflavin T solution at a wavelength near 440 nm and at a wavelength near 480 nm and determining whether or not a fluorescence ratio resulting from dividing the fluorescence intensity at a wavelength of 440 nm by the fluorescence intensity at a wavelength of 480 nm is within a range of 0.4 to 1.0, which is a background level, and when it is determined that the fluorescence ratio does not reach the background level, the step of bringing and the step of separating are further carried out for the thioflavin T solution,
wherein the pure thioflavin T is a thioflavin T reagent having no fluorescence at a peak wavelength near 400 nm.

2. The method according to claim 1, wherein the step of bringing and the step of separating are carried out in a state in which light with a wavelength of 475 nm or lower is blocked.

3. The method according to claim 1, wherein the polar solvent is selected from the group consisting of an aqueous solvent, methanol, ethanol, acetonitrile, and dimethyl sulfoxide, and a mixture solvent in which two or more types thereof are mixed with each other.

4. The method according to claim 1, wherein the non-polar polymeric porous body is a porous body which is formed of a polymer selected from the group consisting of polyvinylidene fluoride (PVDF), polysulfone, polyether sulfone, nylon, cellulose acetate, and nitrocellulose, and two or more types thereof.

5. The method according to claim 1, wherein the non-polar polymeric porous body is a non-polar polymer membrane, and the step of bringing the thioflavin T solution into contact with the non-polar polymeric porous body; and the step of separating the thioflavin T solution after the contact from the non-polar polymeric porous body are carried out by filtering the thioflavin T solution through the non-polar polymer membrane.

6. A method for producing pure thioflavin T comprising a step of carrying out the method according to claim 1.

* * * * *